United States Patent [19]

Gunkel

[11] 4,350,595

[45] Sep. 21, 1982

[54] SEPARATION COLUMN FOR LIQUID CHROMATOGRAPHY AND SEALING ARRANGEMENT THEREFOR

[75] Inventor: Werner Gunkel, Wingerstweg, Fed. Rep. of Germany

[73] Assignee: Merck Patent Gesellschaft mit Beschränkter Haftung, Darmstadt, Fed. Rep. of Germany

[21] Appl. No.: 270,717

[22] Filed: Jun. 5, 1981

[30] Foreign Application Priority Data

Jun. 6, 1980 [DE] Fed. Rep. of Germany ....... 3021366

[51] Int. Cl.$^3$ ............................................ B01D 15/08
[52] U.S. Cl. ..................................... 210/656; 55/386; 210/198.2; 210/351; 210/352
[58] Field of Search ................... 210/198.2, 350, 351, 210/352, 656; 55/386

[56] References Cited

U.S. PATENT DOCUMENTS

| | | | |
|---|---|---|---|
| 62,505 | 2/1867 | Simmons | 210/351 |
| 847,518 | 3/1907 | Shiltz | 210/351 X |
| 3,511,377 | 5/1970 | Hrdina | 210/198.2 |
| 3,680,707 | 8/1972 | Zeek | 210/352 |
| 4,093,548 | 6/1978 | Starkenburg | 210/350 |

*Primary Examiner*—John Adee
*Attorney, Agent, or Firm*—Millen & White

[57] ABSTRACT

A separation column for liquid chromatography is adjustably sealed for reducing dead space therein. The separation column is packed and an elastic diaphragm seals one end. There is spherically shaped inert material located between the packing and the elastic diaphragm with a porous frit located between the inert material and the diaphragm. A piston exerts a force on the diaphragm to stretch it longitudinally into the column thereby reducing the dead space. The frit and inert material operate to uniformly distribute the force exerted by the piston.

11 Claims, 2 Drawing Figures

SEPARATION COLUMN FOR LIQUID CHROMATOGRAPHY AND SEALING ARRANGEMENT THEREFOR

BACKGROUND OF THE INVENTION

The invention relates to a separation column for liquid chromatography. Generally, separation columns for liquid chromatography, in particular those having relatively small diameters, are closed tightly with frits after packing for the purpose of reducing the remaining dead volume as much as possible. In chromatographic separation columns having relatively large diameters, however, it has previously not been possible to pack then in such a way that a packing of completely constant volume results. Instead, when eluent is pumped through, the packing is compressed, as a rule, by about 0.5–2% of the column length, depending on the type of packing material and the method of packing.

In addition, a shrinkage of the packing occurs indendently of the column dimensions. More particularly, this shrinkage especially occurs when polar solvents are used due to the solubility of the sorbents in the eluent; said solubility, although small, is nevertheless significant in continuous operation. In columns which are closed tightly by frits on both sides at the end faces, all these effects lead to an increase in the dead volume between the packing and the frit, resulting in a decrease of the separation efficiency of the column. In addition, the increase in dead volume combined with the drying out of the column, which is not avoidable in practice, combines with shocks and formation of cracks to result in the total destruction of the packing.

Proposals have been made in the past to avoid the dead volume by closing the end of the column by means of stoppers capable of being positioned at adjustable heights. Nonetheless, in the case of columns having relatively large diameters, sealing of the stoppers at the periphery of the column raises problems, since the tolerance in diameter variations are required to be very small. Furthermore, whenever columns of glass, and stoppers having polytetrafluoroethylene gaskets are required because of their good resistance to chemicals, this proposal is not feasible in practice because of the risk of fracture.

German Offenlegungsschrift No. 2,655,650 discloses columns in which a dead volume in the column packing is prevented by radial compression of the column. To achieve this, however, the column itself must consist of an elastic material. Therefore, this proposal cannot be applied to conventional columns of metal, glass or a pressure-resistant plastic.

SUMMARY OF THE INVENTION

It is thus an object of the invention to provide a separation column in which the volume shrinkage of the packing can be compensated for without requiring the use of special column materials for this purpose, or an expensive fabrication procedure in order to obtain especially accurate dimensions. In the present invention, this object is achieved by stabilizing the column packing by continuously and uniformly applying pressure with a piston and sealing of the separation column at the upper end face being effected by a flexible diaphragm.

Accordingly, the invention comprises a separation column for liquid chromatography characterized by having a column packing which can be compressed in the longitudinal direction by means of a piston and is sealed on the piston side by a flexible diaphragm.

The advantage of a separation column according to the invention is that the packing is stabilized by the continuous, uniform application of pressure by means of a piston to the surface of the sorbent. Therefore, dead volumes cannot develop even during prolonged use of the column.

A particular advantage of the invention is that, since a flexible membrane sealing the end face of the separation column is used, the invention can be used in all conventional types of columns without requiring that the internal diameters be subject to particularly narrow tolerance variances. The piston which is required only for transmitting the pressure, but does not effect any sealing function, can therefore be adapted within wider tolerances to the column diameter. In particular, because of the flexible diaphragm, sealing does not cause any problems even in the case of relatively large column diameters and relatively high pressures.

BRIEF DESCRIPTION OF THE DRAWINGS

A preferred embodiment of the separation column according to the invention is represented in the drawings in which.

DETAILED DISCUSSION OF THE INVENTION

Figure 1:
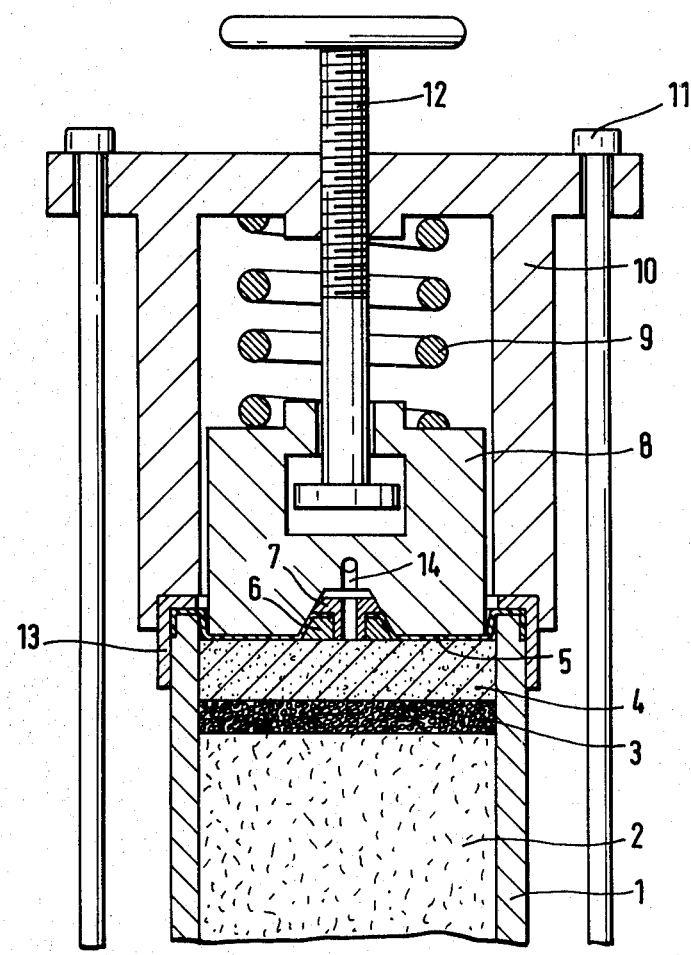
FIG. 1 is a side view in cross section of the top of the column showing a part of the clamping device.
Figure 2:
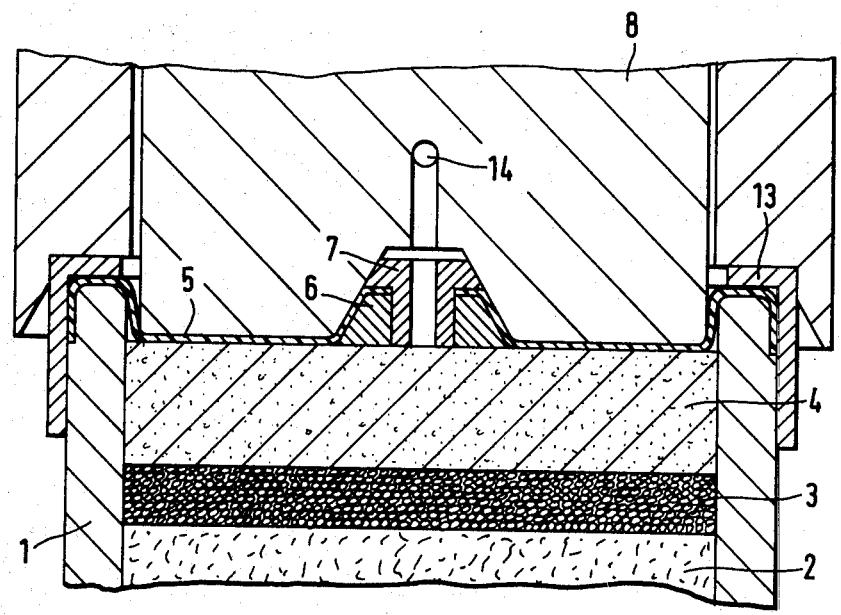
FIG. 2 is an enlarged side view in cross section of the top of the column.

The numeral 1 designates the separation column with column packing 2 located therein. A loose layer 3 in the form of spheres is located therein and a frit 4 is adjacent the layer 3. The flexible diaphragm 5 is joined to the piston 8 by the two component cone 6 and 7. A compression spring 9 is in contact with piston 8. The upper flange 10 of the clamping device for the column is held by the clamping bolts 11. A threaded spindle 12 is connected to the piston 8 for lifting the piston 8 off the column. The ring 13 secures the diaphragm on the column. There is feed channel 14 for the eluent.

The separation columns used can be any of the conventional separation columns, for example those of steel, glass or plastic. The selection of the material here depends in particular on the stresses to which the column is subjected, for example, those resulting from operation at elevated pressure. The invention is preferably used in preparative columns, for example those of about 50–500 mm diameter and greater. The invention is, however, not restricted to columns of this diameter, but can be used favorably in all columns having technically feasible diameters. In particular, separation columns for industrial production which, under certain circumstances, have very large diameters and in which the stability of the packing is even more important than in analytical columns because of the problems attendant thereto, can be manufactured very advantageously in accordance with the present invention. To ensure reliable operation, the only requirement is that the column diameter should be greater than about 1/10 of the column length.

The separation columns according to the invention can be packed with all the conventional sorbents, such as silica gel, kieselguhr or alumina. After the column has been packed, a thin layer 3, for example a layer having a thickness of about 5–10 mm, of an inert material in the form of spheres, preferably of glass, is placed on top. The loose layer 3 of spheres serves to uniformly distribute the pressure exerted by the piston 8. The loose layer 3 of spheres is covered by a frit 4 made of a porous inert material, preferably a porous ceramic material. The frit 4 serves to ensure a uniform distribution of the substances, introduced through the feed channel 14 over the surface of the sorbent. For this purpose, it is also possible to provide distribution channels on the surface of the frit 4. If possible, the separation column 1 should be packed to a height such that the top of the frit 4 is approximately flush with the end face of the separation column 1.

The flexible diaphragm 5 having the two-component joining cone 6 and 7 is then placed on the top of the packed separation column 1 and is secured by means of ring 13. After the column has been inserted into the clamping device, the upper flange 10 is pressed down by means of the clamping bolts 11. In this manner, the flexible diaphragm 5 is securely retained on the end face of the separation column 1 and, at the same time, the column is sealed.

The flexible diaphragm 5, which serves to ensure a reliable seal of the column against the mixtures of substances and the eluents introduced through the capillary 14, must be capable of fully meeting this object even in the case of relatively extensive deformation, for example, as a result of a piston stroke of up to about 15 mm. Suitable materials for this diaphragm are therefore, for example, silicone rubber or butyl rubber. However, because of its very good solvent resistance, coupled with good deformability, polytetrafluoroethylene is particularly preferred as the diaphragm material.

In order to compensate for a volume shrinkage of the column packing 2 while the column is in use, it is only necessary to push the piston 8 further downward by means of a suitable device. Thus, the flexible diaphragm 5 is deformed as shown in the drawings. It is particularly advantageous if the piston 8 is continuously pressed with a predetermined force onto the surface of the sorbent. This can be preferably achieved by providing a compression spring 9 which is fitted between the flange 10 and the piston 8. With the aid of the threaded spindle 12, the piston 8 can be lifted off the column against the pressure of the spring 9; this is necessary for example, during the assembly or dismantling of the separation column.

The present invention relates to an innovation in the design of the column head. The remaining components of the separation column according to the invention, which are not described here, correspond to conventional embodiments familiar to those skilled in the art.

Thus, the invention makes separation columns available which, because the packings are compressed and free from dead volume, allow carrying out optimum separations over a long period of time.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A separation column for liquid chromatography containing compressible column packing therein, said separation column comprising:
   flexible seal means fixedly secured to one end of the column for sealing the packing containing column; and
   compression means operatively associated with said flexible seal means for compressing said compressible column packing to reduce dead volume therein whereby said compression means exerts a force on said flexible seal means to cause stretching thereof into the column for reducing dead volume within the column while said flexible seal means remain secured to said one end of the column.

2. A separation column as in claim 1 wherein said flexible seal means comprises an elastic diaphragm.

3. A separation column as in claim 2 wherein said elastic diaphragm is made of polytetrafluoroethylene, silicone rubber or butyl rubber.

4. A separation column as in claim 1 or 3, further comprising a compression spring associated with and engaging said compression means for exerting a predetermined pressure on said compression means and on the packing contained in the column.

5. A separation column as in claim 1 further comprising a loose layer of spherically shaped inert material located between said flexible seal means and the packing contained in the column, and a porous frit located between said layer of spherically shaped inert material and said flexible seal means.

6. A sealing arrangement for a separation column for liquid chromatography comprising:
   flexible diaphragm means adapted for being fixedly secured at the end of a separation column for sealing the column when filled with column packing; and
   piston means operatively associated with said flexible diaphragm means for compressing the column packing when said sealing arrangement is mounted on a column with said flexible diaphragm means being maintained fixedly secured at the end of a column.

7. A sealing arrangement as in claim 6 wherein said flexible diaphragm means is made of polytetrafluoroethylene, silicone rubber or butyl rubber.

8. A sealing arrangement as in claim 6 or 7 further comprising a compression spring associated with and engaging said piston means for exerting a predetermined pressure on said piston means and the packing contained in the column.

9. A sealing arrangement as in claim 6 further comprising a loose layer of spherically shaped inert material located between said flexible diaphragm means and the packing contained in the column, and a porous frit located between said layer of spherically shaped inert material and said flexible diaphragm means.

10. A method of sealing a separation column for liquid chromatography whereby dead space in the column can be substantially reduced, the method comprising the steps of:
   sealing the column after packing with an elastic diaphragm by fixedly securing the elastic diaphragm at one end thereof; and
   compressing the elastic diaphragm longitudinally into the column by exerting a force on the elastic diaphragm with a compressing piston while maintaining the elastic diaphragm fixedly secured to the end of the column.

11. A method as in claim 10 further comprising the steps of placing a loose layer of spherically shaped inert material in the column on top of the packing, and placing a porous frit on top of the loose layer of spherically shaped inert material prior to performing said sealing step.

* * * * *